United States Patent [19]

Donovan

[11] Patent Number: 5,560,377
[45] Date of Patent: Oct. 1, 1996

[54] DENTAL FLOSS

[76] Inventor: Marion Donovan, 850 Park Ave., New York, N.Y. 10021

[21] Appl. No.: 421,747

[22] Filed: Apr. 13, 1995

[51] Int. Cl.⁶ .................................................. A61C 15/00
[52] U.S. Cl. ........................................ 132/321; 132/329
[58] Field of Search ................................ 132/321, 323, 132/329

[56] References Cited

U.S. PATENT DOCUMENTS

| | | | |
|---|---|---|---|
| 3,789,858 | 2/1974 | Pesce | 132/321 |
| 4,523,600 | 6/1985 | Donovan | 132/321 |
| 4,798,216 | 1/1989 | McCarty et al. | 132/321 |
| 4,832,063 | 5/1989 | Smole | 132/321 |
| 5,063,948 | 11/1991 | Lloyd | 132/321 |
| 5,094,255 | 3/1992 | Ringle | 132/321 |
| 5,311,889 | 5/1994 | Ringle et al. | 132/321 |

Primary Examiner—Cary E. O'Connor
Attorney, Agent, or Firm—George M. Gould

[57] ABSTRACT

The present disclosure relates to an improved floss implement comprising a composite of a multifilament yarn bonded to an extruded monofilament. Both elements are made of polymer compounds, preferably nylon, to provide desired ease of use of the monofilament as a leader to pass the implement easily between the teeth or under bridges while the multifilament yarn can be provided in looped embodiments, as a bush element or in the form of one or more tails thus providing superior flossing action when passed between the teeth or under bridges.

9 Claims, 4 Drawing Sheets

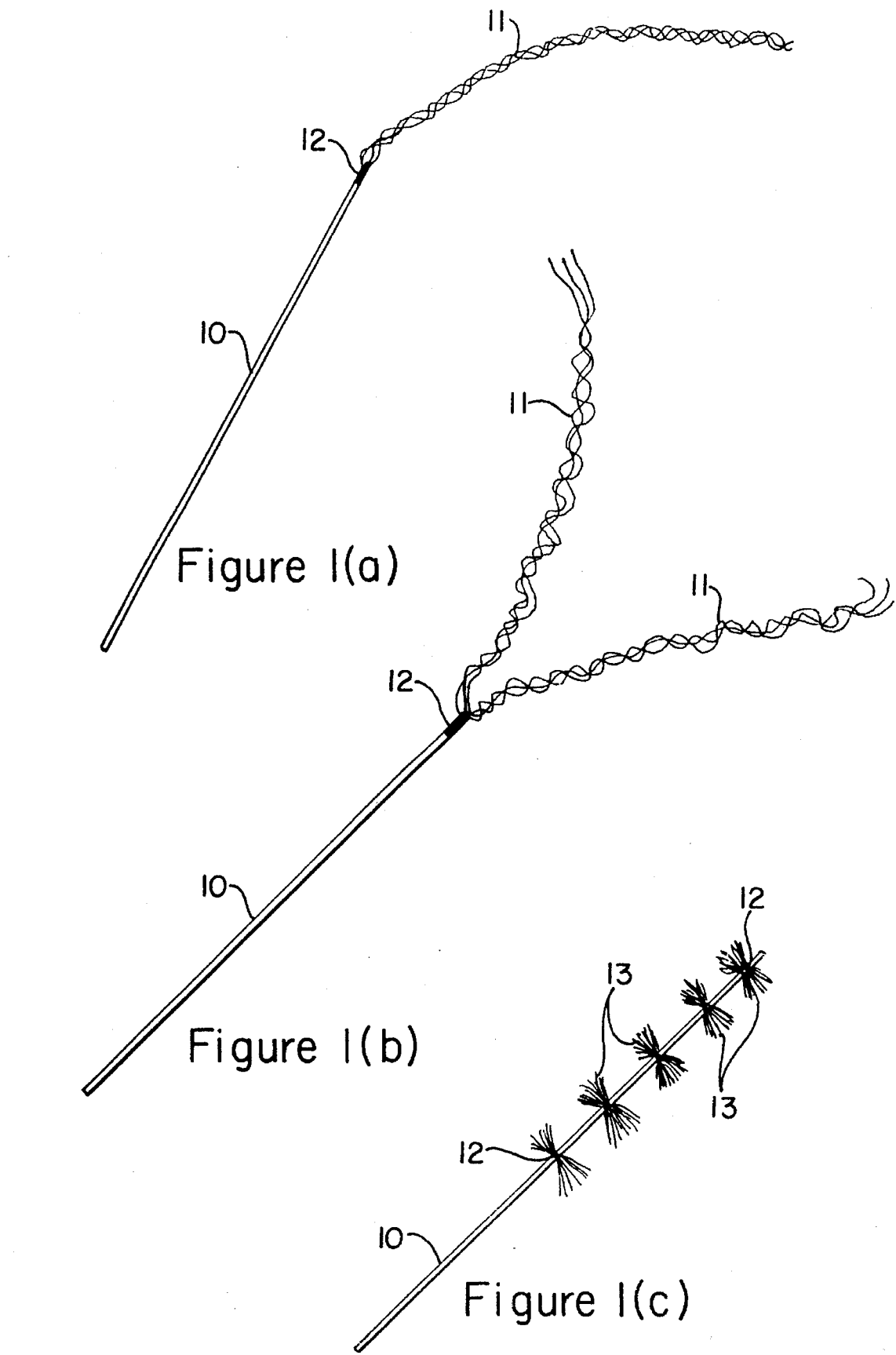

DENTAL FLOSS

BACKGROUND AND SUMMARY OF THE INVENTION

It is generally recognized in the dental profession that plaque which remains on the teeth after brushing is a major cause of tooth and gum problems and that flossing is the only effective process for individuals to remove that plaque. Unfortunately, flossing is not as popular as it should be, particularly among children, probably because of the difficulty and inconvenience of using known flossing products and techniques.

The most common commercial floss product is a multifilament thread of considerable length, e.g., 50 or 100 yards, wound on a packaged spool. Use of this product involves pulling an appropriate section of thread from the package, severing the withdrawn section and wrapping its ends about two fingers on opposite hands, and then working the section in the inter tooth spaces while maintaining it in a taut state. These manipulations require a degree of dexterity which make the flossing process unattractive to many people and very difficult for most children. In addition, maintenance of the tension required for effective plaque removal causes the thread to bind and tend to cut the user's fingers. Moreover, renewal of the active portion of the thread, if it should become frayed as flossing proceeds, necessitates the further inconvenient manipulation of unwinding thread from one finger and winding it onto the other finger, Finally, the packaged spools are somewhat bulky, so carrying the floss in a pocket or in a handbag is a burden. As a result, frequent use of the floss is discouraged.

A solution to many of these problems existing in the flossing products of the prior art was provided in my earlier invention described and claimed in U.S. Pat. No. 4,523,600. In that case I provided an improved dental floss comprising a multifilament thread forming a flossing loop which may be joint-free and comprise many turns of a single, continuous filament or it may be made from multifilament thread and has a joint formed by gluing, heat sealing, knotting or air splicing. The latter type loop can include at least one protruding tail which performs a mopping function during plaque removal.

During flossing procedure, as one section of floss has done its cleaning, a fresh section can be easily rotated into use without rewinding and unwinding floss from one hand onto the other. Because it is a relatively small device, a loop of floss can be handily rinsed during the cleaning procedure (as a person rinses the toothbrush frequently when brushing teeth).

A more recent improved commercial format has been marketed under the trademark Oral B Superfloss which provides precut lengths of floss comprising a short leader section of single stranded, relatively stiff multifilament thread, a central section of entangled strands of multifilament threads of greater cross-sectional area than the leader section and a trailing length of a single strand of multifilament thread which serves as the anchoring end which can be wrapped around the fingers to provide support for the flossing action around the teeth.

A further alternative is taught by Ringle in U.S. Pat. No. 5,094,255, filed Feb. 8, 1989 and issued Mar. 10, 1992. In that patent a dental floss implement is made from a shaped multifilament acrylic fiber (preferably three and four filament threads are used) where a portion of the fiber can be modified by treatment with one or more of the following: solvent, embedding plastic, heat, pressure or tension.

It is therefore the purpose of the present invention to provide improved flossing composite constructs that allow the user to benefit from the advantages of a relatively rigid monofilament element which can function as an efficient leader sequence which can allow easy passage between the teeth and bonded to such element a multifilament section which can be provided in multiple forms to assist the cleaning action and to provide user support when provided in various looped forms. The composite is readily formed by bonding the multifilament thread or yarn and the extruded monofilament element using methods well known in the art such as, for example, electronic welding, or welding with a suitable glue or adhesive or by air splicing. Such procedures allow the floss composites of the present invention to be produced using existing production equipment thus providing facile production, packaging and withdrawal of the product from the dispensing container. As was pointed out in my earlier patent (U.S. Pat. No. 4,523,600) the presence of one or more tails is useful in the flossing procedure as it serves a mopping function when passing between the teeth. In addition the composites of the present invention provide leader portions which are of simple construction avoiding the complex steps needed in U.S. Pat. No. 5,094,255 to convert the acrylic multifilament thread into the leader section.

BRIEF DESCRIPTION OF THE DRAWING

Several embodiments of the invention are described herein with reference to the accompanying drawing, in which:

FIGS. 1a, 1b and 1c are perspective view of several versions of the improved, composite floss of the present invention in toothpick-like modes where the multifilament component can be optionally constructed in the form of a single, long tail (1a), two tails (1b) or as spaced, fluffy surfaces (1c).

DESCRIPTION OF THE PREFERRED EMBODIMENTS

Figure 2A:
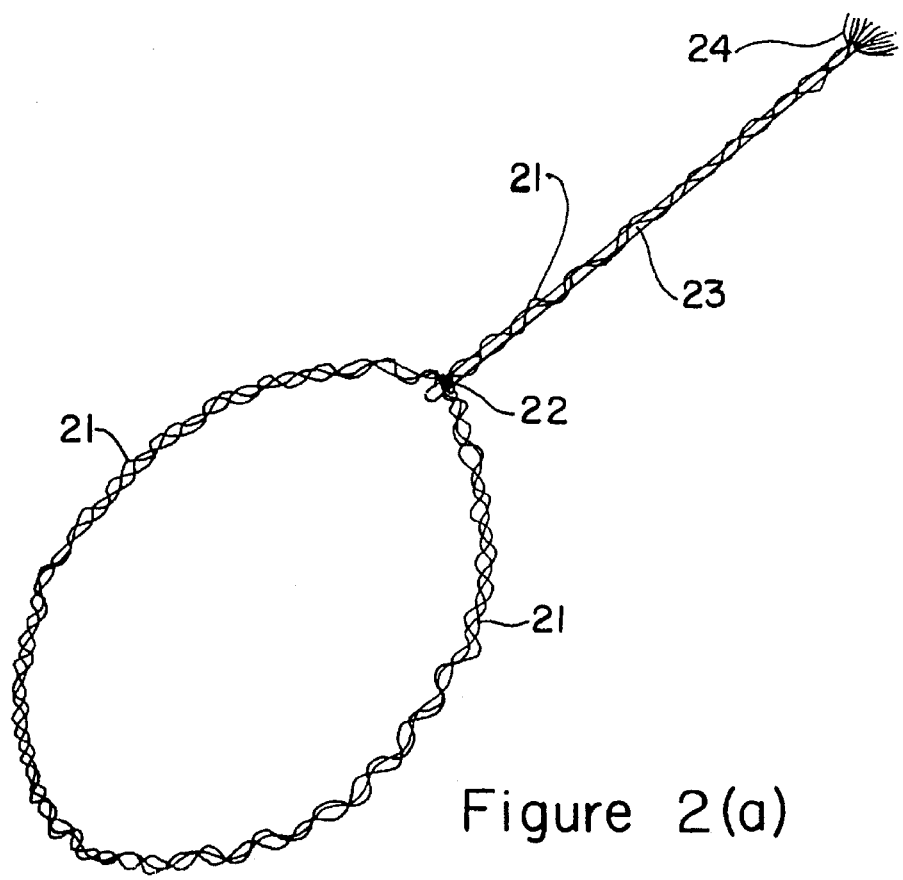
FIGS. 2a and 2b are a perspective view showing the improved, composite floss of the present invention in loop modes where the multifilament component can be optionally constructed in loop form at one distal end of the monofilament thread and can be provided as a brush form at the other end of the monofilament thread (2a), or in loop format joined at an internal point of the extruded monofilament element (2b).

Referring to FIG. 1, several versions of the improved composite flossing product of the present invention in a toothpick like modality are shown. In the embodiment depicted in FIG. 1(a) a toothpick-like composite is provided by using a monofilament leader element 10 which is bonded at one end 12 by welding to a multifilament thread 11. The monofilament leader 10 can be passed easily between the teeth or a bridge and the multifilament element can be pulled through to provide a brushing action which dislodges food particles and plaque in a highly efficient manner. Alternative constructs of the toothpick-like embodiments are provided in FIGS. 1(b) and 1(c). Thus, in FIG. 1(b) the extruded monofilament leader element 10 is provided at one end with two multifilament yarn elements 11 which are welded to leader element 10 at point 12. This format provides enhanced brushing action but would be somewhat more difficult to pass between the teeth than the embodiment in FIG. 1(a). FIG. 1(c) shows an embodiment which is particularly easy to pass between closely spaced teeth or tight bridgework. In such embodiment monofilament leader element 10 is provided with spaced multifilament yarn tufts 13. While two such tufts are shown in the figure, it is understood that such number is optional and additional tufts may be utilized to provide additional brushing action when the composite implement is passed between the teeth.

FIG. 2 provides two embodiments which provide a multifilament loop attached to a monofilament leader. In FIG. 2(a) the multifilament yarn forms a loop 21 attached to one end of the monofilament element 23 at weld 22. The multifilament yarn continues along the entire length of the extruded monofilament element and at its other end forms a small bush 24. In operation, this embodiment allows the user to pass the bush element between the teeth using the underlying monofilament element as support to provide an initial flossing action. After the leader is passed through the teeth space or under the bridge, the loop element is then engaged by the fingers and passed back and forth in a conventional flossing motion.

Figure 2B:
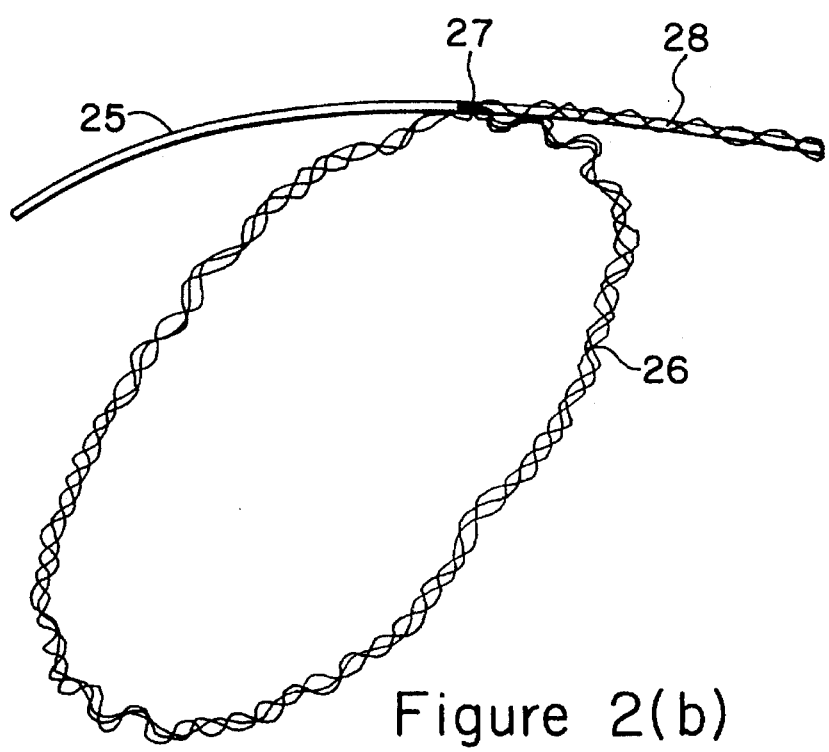

The second embodiment of FIG. 2 is shown in FIG. 2(b). In this embodiment of the loop version of the composite floss device of the present invention the multifilament loop element 26 is welded at point 27 which is at a midpoint of monofilament leader element 25. Both elements are bonded together to form a composite tail element 28. Again in operation the monofilament lead element 25 allows for easily guided insertions between the teeth. The loop element can then be engaged by the user's fingers to allow the loop to be moved back and forth between the teeth in a proper flossing action. When the flossing implement is removed from the teeth, the tail element will serve as a further floss aid.

Figure 3:
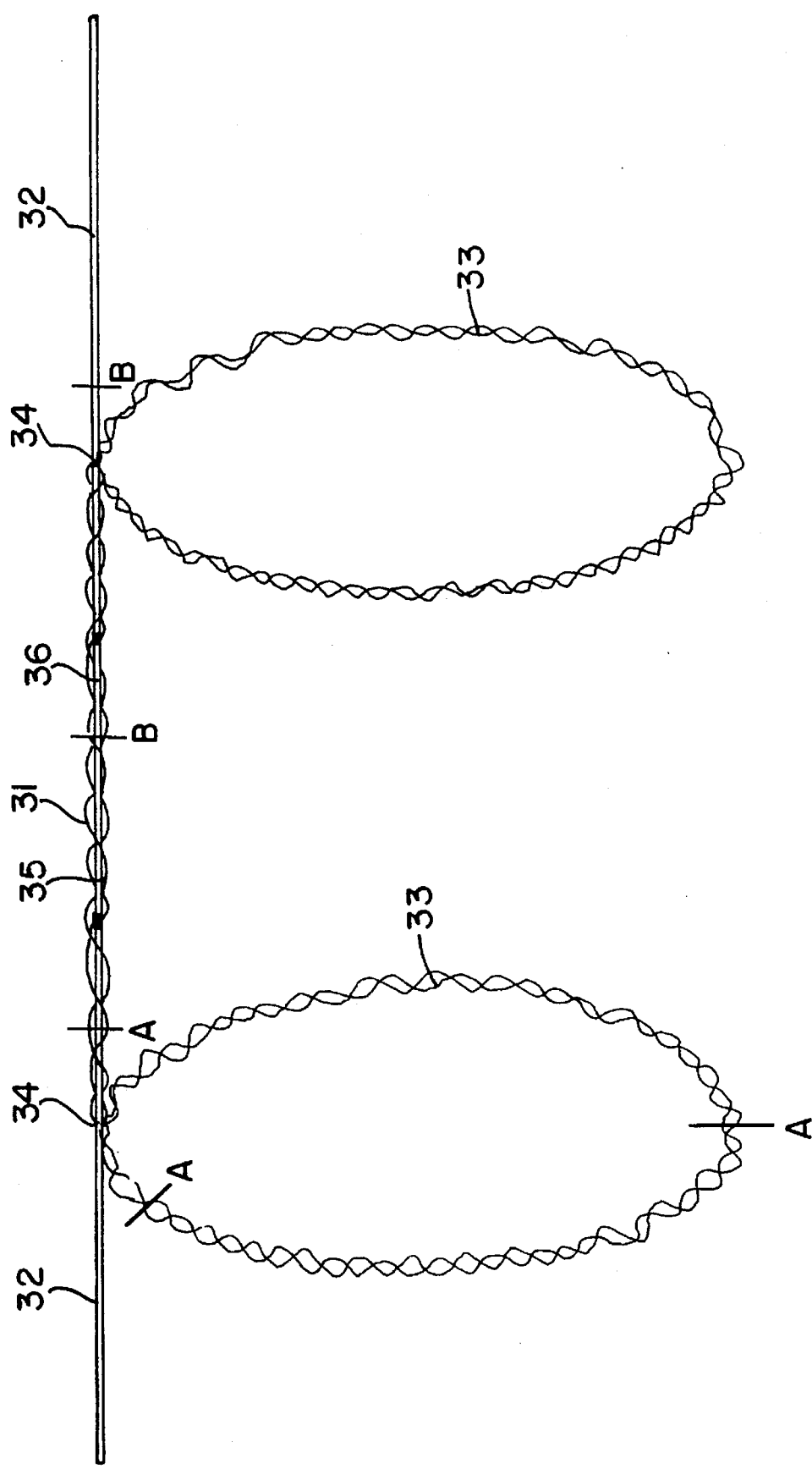
FIG. 3 is a perspective view of a manufacturing process intermediate state showing multiple multifilament yarn loops welded to the extruded monofilament element which can be clipped at selected points to provide the various embodiments of the instant invention described in the earlier figures.

The composite floss constructs of the present invention can be produced using methods known per se in the flossing art, such as, for example, by modification to the methods described in U.S. Pat. No. 4,523,600. One suitable methodology for production of the various embodiments of the instant invention is illustrated FIG. 3. In the preferred production process a multifilament thread 31 and an extruded monofilament 32 are passed in parallel through a suitable splicing or bonding head. As seen in FIG. 3 the length of the multifilament yarn is substantially longer than the length of the monofilament so the multifilament yarn can form continuous loops 33 along the length of monofilament 32. The loops are then bonded to the monofilament at a desired point 34 or points 35, 36 and the resulting composite construct is then clipped at selected places to provide the various embodiments shown in FIGS. 1 and 2.

Thus, clipping the composite constructs at the places shown by line —A—will result in the preparation of the toothpick-like embodiment seen in FIG. 1(a). By clipping the composite constructs at the places shown by line —B—will result in the preparation of the loop embodiment shown in FIG. 2 (a). It is, of course, within the skill of person knowledgeable in the floss art to modify the cutting and bonding points in the manner indicated above to provide any of the composite embodiments which are contemplated by the present invention. Thus, the multifilament yarn can be bonded at a single point shown to produce the embodiments provided in FIG. 1 or the bonding can extend over lengths of the monofilament thread to provide the embodiments shown in FIG. 2.

Although it is preferred that the composite elements in the FIG. 3 embodiments be joined by welding in a manner known per se, it should be evident that any of the other joining techniques mentioned above may be used.

It should be evident that, if desired, the manufacturing techniques represented by FIG. 3 may involve use of multiple loop-forming stations so that a plurality of loops can be made simultaneously.

Figure 4A:
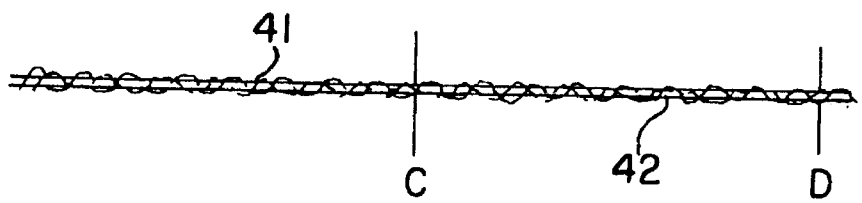
FIGS. 4a, 4b and 4c are perspective views of an alternative manufacturing process showing one monofilament thread joined to one multifilament yarn by spaced bondings or welds in various stages of operation.

In FIG. 4(a) there is shown one monofilament thread 41 joined to a multifilament yarn 42 as it is formed from the manufacturing machine. The joining occurs at points C and D by welding or bonding. The product in this form can be used as a toothpick floss for cleaning under bridges and in tight spaces. Cuts can be made at C and D after bonding.

Figure 4B:
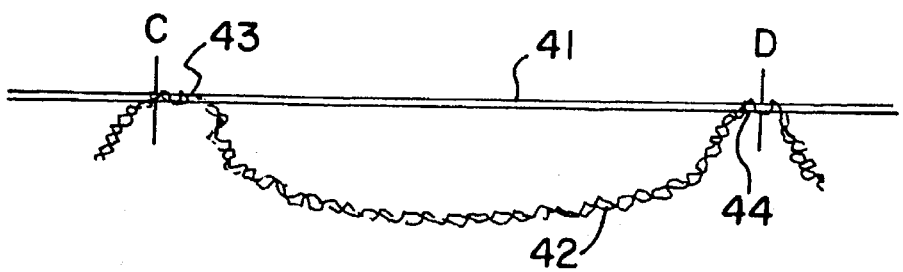

A further format is shown in FIG. 4(b) where the end bonds are seen as points 43 and 44 at either end of the floss device and the multifilament yarn 42 is pulled away at its center portion. This allows the user to twirl the leader to thicken the floss as it encircles the monofilament thread to thicken it and provide more bulk to clean the various sizes of spaces in the mouth.

Figure 4C:
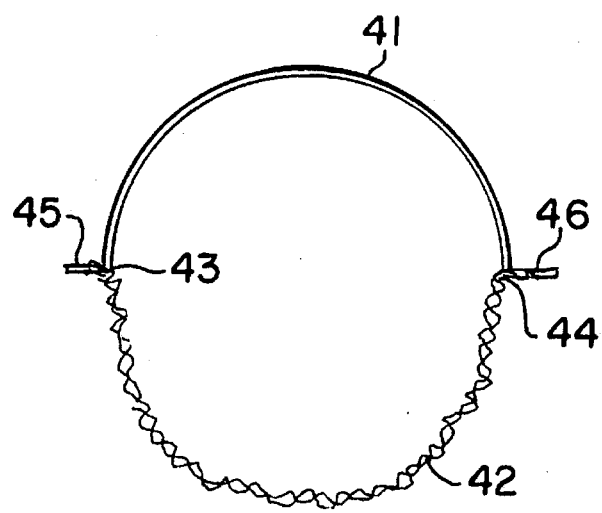

Finally in FIG. 4(c) the floss device is shown in the form of a full circle where the stretchy multifilament 42 can be utilized in flossing normal teeth. By selecting the cut points at C and D leader portions 45 and 46 can be formed and used if there is a stoppage of some sort between teeth. The leader can get the floss through at the gum line and the multifilament yarn 42 can be lifted away by itself and passed through the space between the teeth until the stoppage is cleaned out.

The extruded monofilaments used in the composite flossing implements of the present invention are preferably made of polymeric materials such as nylon. A suitable dental grade nylon for this purpose is commercially available as a 612 type nylon extruded monofilament which is clear and transparent under the trademark Tynex (DuPont).

The multifilament yarn used in the composite flossing implements of the present invention are also preferably made of a polymer such as nylon threads. A preferred multifilament yarn is comprised of about 272 fine nylon filaments (800 denier). A commercially available nylon fiber, manufactured by DuPont is a solid organic polymer composed of carbon, hydrogen, nitrogen, and oxygen. The DuPont multifilament polyamide nylon and FDA colors used in preparing this stretchy, texturized floss yarn are totally compliant with the DuPont Material Safety Data Sheets (MSDS).

Another multifilament yarn used in some of the aspects of this invention wherein a textured fluffy yarn can be paired with another yarn, not textured, is described by its manufacturer, Belding Corticelli as #2666 natural, bonded, nylon dental floss, shred resistant. The nominal denier is 170, the actual denier is 540–600, with 1.0 to 5.0 turns to the inch.

It is contemplated that in the case of loops the present invention be provided in various sizes, e.g., a 3½" circumference for use by small children, and circumferences of 5", 6" and 8" for use by older children and adults. However, it is understood that there are no practical limitations on the size of the loops and they are constructed to meet the requirements of the user.

In dental floss nylon yarns have many advantages over acrylic fibers or plastics in general. Acrylic is a spun yarn whereas nylon is a continuous filament and not spun from many short fibers. Nylon is strong and will not break apart. Nylon has a stretch capability whereas a spun yarn does not. Because of its stretch, and having been texturized nylon is soft and gentle when flossing around the gumline, and because of its capacity to take on moisture, it can carry medications prescribed by dentists for treatment of gumline disease to the exact spot where such medication is needed.

I claim:

1. An improved composite flossing implement comprising a monofilament element so arranged and constructed so as to form a floss leader means having a first and a second end, said leader means being adapted for ready access between the teeth, said monofilament element having one or more multifilament elements bonded thereto in a manner selected from one of the following:
   (a) said multifilament element is bonded to one of said ends of said monofilament element and extends outwardly therefrom in an essentially non-overlapping manner;
   (b) at least two multifilament elements are bonded in spaced relation along the length of said monofilament element; or
   (c) said multifilament element is provided in the form of a loop.

2. The improved floss implement of claim 1, wherein said monofilament element and said multifilament element are both made of nylon.

3. The improved floss element of claim 2 wherein said monofilament element is made of an extruded nylon.

4. The improved floss implement of claim 2 wherein at least two multifilament thread elements are bonded in spaced relation along the length of said monofilament element, said multifilament elements being formed in bush-like shape to afford flossing action when engaged with said teeth.

5. The improved floss implement of claim 2 wherein a said multifilament element is bonded to one end of said monofilament element and is formed in at least one tail like shape.

6. The improved floss implement of claim 5 wherein said multifilament element is formed into two tail like parts.

7. The improved floss implement of claim 2 wherein said multifilament element is provided in the form of a loop which is so arranged and constructed to be engageable by the fingers of the user to assist in manipulation of the implement when engaged with said teeth.

8. The improved floss implement of claim 7 wherein said loop is provided at one end of said monofilament element, said multifilament thread element is bonded to the length of said monofilament element and extends beyond the second end thereof to form a bush means at said second end.

9. The improved floss implement of claim 7 wherein said loop is bonded to said monofilament element at a midpoint, one end of said monofilament element is uncovered and forms a leader means and the other end of said monofilament element is bonded to said multifilament thread element to provide a composite leader means.

\* \* \* \* \*